United States Patent
Henderson et al.

(10) Patent No.: US 6,491,699 B1
(45) Date of Patent: Dec. 10, 2002

(54) INSTRUMENT GUIDANCE METHOD AND SYSTEM FOR IMAGE GUIDED SURGERY

(75) Inventors: Jaimie Henderson, St. Louis, MO (US); Richard D. Bucholz, St. Louis, MO (US); Kurt R. Smith, Eldorado Springs, CO (US); Kevin J. Frank, Lafayette, CO (US); John B. Clayton, Supeior, CO (US); Catalina J. Carroll, Memphis, TN (US); Phillip T. Ulberg, Reno, NV (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 0 days.

(21) Appl. No.: 09/557,004

(22) Filed: Apr. 20, 2000

Related U.S. Application Data

(60) Provisional application No. 60/130,118, filed on Apr. 20, 1999.

(51) Int. Cl.[7] .............................................. A61B 19/00
(52) U.S. Cl. ...................................... 606/130; 600/414
(58) Field of Search .................... 606/1, 130; 600/117, 600/118, 414, 417, 427, 429

(56) References Cited

U.S. PATENT DOCUMENTS

| | | | | |
|---|---|---|---|---|
| 3,073,310 A | * | 1/1963 | Mocarski | 606/130 |
| 4,058,114 A | | 11/1977 | Soldner | 128/2 V |

(List continued on next page.)

FOREIGN PATENT DOCUMENTS

| | | |
|---|---|---|
| DE | 197 15 202 A1 | 4/1997 |
| DE | 197 47 427 A1 | 10/1997 |

(List continued on next page.)

OTHER PUBLICATIONS

Hahn et al., Needle Biopsy of Intracranial Lesions Guided by Computerized Tomography, Neurosurgery, Jul. 1979, 11–15, vol. 5, Part 1.

(List continued on next page.)

Primary Examiner—Anhtuan T. Nguyen
Assistant Examiner—Michael M Thompson
(74) Attorney, Agent, or Firm—Harness, Dickey & Pierce, P.L.C.

(57) ABSTRACT

Generally, the present invention is directed to a method and system for a aligning surgical guide instrument over a burr hole in a patient's body. More particularly, the present invention is directed to a stand-alone instrument guidance unit that is attachable to a patient's skull. Adjustments of a surgical instrument can be made in x, y, z, and angular directions using the system and method of the present invention. In one aspect of the present invention, an instrument guide unit includes an instrument guide for guiding a surgical instrument into the body of a patient and a base unit operative to be secured to the body in an area in which surgery. is to occur. The base unit is coupled to the instrument guide. An adjustment mechanism, coupled to the base unit and the instrument guide, is operative to adjust the instrument guide in lateral directions with respect the surface of the area. The adjustment mechanism is operative to adjust the instrument guide in x and y directions. The adjustment mechanism includes an x direction control mechanism for adjusting the instrument in an x direction and a y direction control mechanism for adjusting the instrument in a y direction. The y direction control mechanism may be coupled to the x direction control mechanism. The positional movement of the surgical instrument in the z direction may be tracked by sensing the location of a transducer coupled to the surgical instrument.

8 Claims, 9 Drawing Sheets

U.S. PATENT DOCUMENTS

| | | | |
|---|---|---|---|
| 4,182,312 A | 1/1980 | Mushabac | 433/68 |
| 4,232,338 A | 11/1980 | Netravali et al. | |
| 4,465,069 A | 8/1984 | Barbier et al. | 128/303 B |
| 4,583,538 A | 4/1986 | Onik et al. | 128/303 B |
| 4,602,622 A | 7/1986 | Bär et al. | 128/303 B |
| 4,608,977 A | 9/1986 | Brown | 128/303 B |
| 4,638,798 A | 1/1987 | Shelden et al. | 128/303 B |
| 4,673,352 A | 6/1987 | Hansen | 433/69 |
| 4,686,977 A | 8/1987 | Cosma | 128/207.17 |
| 4,686,997 A | 8/1987 | Oloff et al. | 128/653 |
| 4,723,544 A | 2/1988 | Moore et al. | 128/303 B |
| 4,727,565 A | 2/1988 | Ericson | 378/205 |
| 4,733,661 A | 3/1988 | Palestrant | 128/303 B |
| 4,750,487 A | 6/1988 | Zanetti | 128/303 B |
| 4,776,749 A | 10/1988 | Wanzenberg et al. | 414/680 |
| 4,805,615 A | 2/1989 | Carol | 128/303 B |
| 4,809,694 A | 3/1989 | Ferrara | 128/303 B |
| 4,841,967 A | 6/1989 | Chang et al. | 128/303 B |
| 4,875,478 A | 10/1989 | Chen | 128/303 B |
| 4,931,056 A | 6/1990 | Ghajar et al. | 606/130 |
| 4,952,214 A | 8/1990 | Comparetto | 606/87 |
| 4,955,891 A | 9/1990 | Carol | 606/130 |
| 5,047,036 A | 9/1991 | Koutrovelis | 606/130 |
| 5,078,140 A | 1/1992 | Kwoh | 128/653.1 |
| 5,116,345 A | 5/1992 | Jewell et al. | 606/130 |
| 5,186,174 A | 2/1993 | Schlöndorff et al. | 128/653.1 |
| 5,198,877 A | 3/1993 | Shulz | 356/375 |
| 5,257,998 A | 11/1993 | Ota et al. | 606/130 |
| 5,279,309 A | 1/1994 | Taylor et al. | 128/782 |
| 5,305,203 A | 4/1994 | Raab | 364/413.13 |
| 5,309,913 A | 5/1994 | Kormos et al. | 128/653.1 |
| 5,383,454 A | 1/1995 | Bucholz | 128/653.1 |
| 5,389,101 A | 2/1995 | Heilbrun et al. | 606/130 |
| 5,399,146 A | 3/1995 | Nowacki et al. | 601/4 |
| 5,402,801 A | 4/1995 | Taylor | 128/898 |
| 5,447,154 A | 9/1995 | Cinquin et al. | 128/653.1 |
| 5,483,961 A | 1/1996 | Kelly et al. | 128/653.1 |
| 5,494,034 A | 2/1996 | Schlöndorff et al. | 128/653.1 |
| 5,515,160 A | 5/1996 | Schulz et al. | 356/241 |
| 5,517,990 A | 5/1996 | Kalfas et al. | 128/653.1 |
| 5,531,227 A | 7/1996 | Schneider | 128/653.1 |
| 5,531,520 A | 7/1996 | Grimson et al. | 382/131 |
| 5,551,429 A | 9/1996 | Fitzpatrick et al. | 128/653.1 |
| 5,568,809 A | 10/1996 | Ben-haim | 128/656 |
| 5,572,999 A | 11/1996 | Funda et al. | 128/653.1 |
| 5,588,430 A | 12/1996 | Bova et al. | 128/653.1 |
| 5,603,318 A | 2/1997 | Heilbrun et al. | 128/630 |
| 5,617,857 A | 4/1997 | Chader et al. | 128/653.1 |
| 5,622,170 A | 4/1997 | Schulz | 128/653.1 |
| 5,630,431 A | 5/1997 | Taylor | 128/897 |
| 5,638,819 A | 6/1997 | Manwaring et al. | 128/653.1 |
| 5,643,286 A | 7/1997 | Warner et al. | 606/130 |
| 5,647,361 A | 7/1997 | Damadian | 128/683.2 |
| 5,662,111 A | 9/1997 | Cosman | 128/653.1 |
| 5,676,673 A | 10/1997 | Ferre et al. | 606/130 |
| 5,682,886 A | 11/1997 | Delp et al. | 128/653.1 |
| 5,695,500 A | 12/1997 | Taylor et al. | 606/130 |
| 5,695,501 A * | 12/1997 | Carol et al. | 606/130 |
| 5,711,299 A | 1/1998 | Manwaring et al. | 128/653.1 |
| 5,748,767 A | 5/1998 | Raab | 382/128 |
| 5,749,362 A | 5/1998 | Funda et al. | 128/653.1 |
| 5,755,725 A | 5/1998 | Druais | 606/130 |
| 5,772,594 A | 6/1998 | Barrick | 600/407 |
| 5,776,064 A * | 7/1998 | Kalfas et al. | 600/417 |
| 5,795,294 A | 8/1998 | Luber et al. | 600/407 |
| 5,799,055 A | 8/1998 | Peshkin et al. | 378/42 |
| 5,800,535 A | 9/1998 | Howard, III | 623/10 |
| 5,810,712 A | 9/1998 | Dunn | 600/114 |
| 5,817,106 A | 10/1998 | Real | 606/130 |
| 5,823,958 A | 10/1998 | Truppe | 600/426 |
| 5,833,608 A | 11/1998 | Acker | 600/409 |
| 5,833,672 A | 11/1998 | Shmulewitz et al. | 600/562 |
| 5,833,709 A | 11/1998 | Rise et al. | 607/2 |
| 5,834,759 A | 11/1998 | Glossop | 250/203.1 |
| 5,836,954 A | 11/1998 | Heilbrun et al. | 606/130 |
| 5,848,967 A | 12/1998 | Cosman | 600/426 |
| 5,851,183 A | 12/1998 | Bucholz | 600/425 |
| 5,868,675 A | 2/1999 | Henrion et al. | 600/424 |
| 5,871,445 A | 2/1999 | Bucholz | 600/407 |
| 5,871,487 A | 2/1999 | Warner et al. | 606/130 |
| 5,891,157 A | 4/1999 | Day et al. | 606/130 |
| 5,904,691 A | 5/1999 | Barnett et al. | 606/130 |
| 5,920,395 A | 7/1999 | Schulz | 356/375 |
| 5,921,922 A | 7/1999 | Costales et al. | 606/130 |
| 5,921,992 A * | 7/1999 | Costales et al. | 606/130 |
| 5,984,930 A | 11/1999 | Maciunas et al. | 606/130 |
| 6,021,343 A * | 2/2000 | Foley et al. | 600/417 |

FOREIGN PATENT DOCUMENTS

| | | |
|---|---|---|
| EP | 0 359 773 B1 | 5/1988 |
| EP | 0 207 452 A2 | 6/1988 |
| EP | 0 326 768 A2 | 12/1988 |
| EP | 0 427 358 A1 | 10/1990 |
| EP | 0 469 966 A1 | 7/1991 |
| EP | 0 919 202 A2 | 6/1999 |
| EP | 0 919 203 A2 | 6/1999 |
| GB | 2 094 590 | 2/1982 |
| WO | WO 88/0915 | 12/1988 |
| WO | WO 91/04711 | 4/1991 |
| WO | WO 91/07726 | 5/1991 |
| WO | WO 92/06645 | 4/1992 |
| WO | WO 94/23647 | 10/1994 |
| WO | WO 94/24933 | 11/1994 |
| WO | WO 96/11624 | 4/1996 |
| WO | WO 96/32059 | 10/1996 |
| WO | WO 97/49453 | 12/1997 |
| WO | WO 99/15097 | 4/1999 |

OTHER PUBLICATIONS

Moran et al., Central Nervous System Lesions Biopsied or Treated by CT–Guided Needle Placement, Radiology, Jun. 1979, 681–686, vol. 131, No. 3.

Bergstrom et al., Stereotaxic Computer Tomography, Am J Roentgenol, 1976, 167–170, vol. 127.

Troccaz et al., The use of localizers, robots and synergistic devices in CAS.

Kondziolka et al., Guided Neurosurgery Using the ISG Viewing Wand®, Contemporary Neurosurgery, 1995, 1–6, vol. 17, No. 8.

Olivier et al., Frameless stereotaxy for surgery of the epilepsies: preliminary experience. Journal of Neurosurgery, Oct. 1994, 629–633, vol. 81, No. 4.

Smith et al., The Neurostation™—A Highly Accurate, Minimally Invasive Solution to Frameless Stereotactic Neurosurgery, Computerized Medical Imaging and Graphics, 1994, 247, 274–277, vol. 18, No. 4.

Reinhardt et al., Sonic Stereometry in Microsurgical Procedures for Deep–Seated Brain Tumors and Vascular Malformations, Neurosurgery, Jan. 1993, 51–57, vol. 32, No. 1.

Reinhardt, Neuronavigation: A Ten–Year Review, Neurosurgery, ____, 329–341.

Bucholz et al., Intraoperative localization using a three dimensional optical digitizer, Proceedings of Clinical Applications of Modern Imaging Technology, Jan. 1993, 312–322, vol. 1894.

PixSys, Alignment Procedure for the PixSys Two–Emitter Offset Probe for the SAC GP–8–3d Sonic Digitizer, PixSys, Boulder, CO.

Pixsys, 3–D Digitizing Accessories, Pixsys, Boulder, CO.

Adams et al., Orientation Aid for Head and Neck Surgeons, Innov. Tech. Biol. Med., 1992, ___, vol. 13, No. 4.

Reinhardt et al., Microsurgical Removal of Deep–Seated Vascular Malformations Using Sonar Stereometry, Ultraschall in Med., 1991, 80–84, vol. 12.

Pelizzari et al., Interactive 3D Patient–Image Registration, Information Processing in Medical Imaging, 1991, 132–141, Springer–Verlag Berlin Heidelberg, Germany.

Mazier et al., Computer Assisted Interventionist Imaging: Application to the Vertebral Column Surgery, Annual International Conference of the IEEE Engineering in Medicine and Biology Society, 1990, 430–431, vol. 12, No. 1.

Krybus et al., Navigation Support for Surgery by Means of Optical Position Detection, ___, 362–366.

Rosenbaum et al., Computerized Tomography Guided Stereotaxis: A New Approach, Applied Neurophysiology, 1980, 172–173, vol. 43, No. 3–5.

Boethius et al., Stereotaxic computerized tomography with GE 8800 scanner, J. Neurosurg., 1980, 794–800, vol. 52, No. 6.

Yeates et al., Simplified and accurate CT–guided needle biopsy of central nervous system lesions, J. Neurosurg., 1982, 390–393, vol. 57, No. 3.

Heilbrun, Computed Tomography–Guided Stereotactic System, Clinical Neurosurgery, 564–581.

Heilbrun et al., Preliminary experience with Brown–Roberts–Wells (BRW) computerized tomography stereotaxic guidance system, J. Neurosurg., 1983, 217–222, vol. 59.

La Vallee, A New System for Computer Assisted Neurosurgery, IEEE Engineering in Medicine & Biology Society 11$^{th}$ Annual International Conference, 1989, 926–927.

La Vallee et al., Computer Assisted Driving of a Needle into the Brain, Computer Assisted Radiology, 1989, 416–420, Springer–Verlag.

La Vallee, Adaptation de la Methodologie a Quelques Applications Cliniques, Chapter VI, pp. 133–148.

* cited by examiner

INSTRUMENT GUIDANCE METHOD AND SYSTEM FOR IMAGE GUIDED SURGERY

RELATED APPLICATION

This application claims priority benefit to U.S. Provisional Patent Application No. 60/130,118 entitled "Instrument Guidance Method and System For Image Guided Surgery", filed on Apr. 20, 1999.

BACKGROUND OF THE INVENTION

1. Field of the Invention

The present invention relates generally to computer assisted image guided medical and surgical navigation systems that generate images during medical and surgical procedures indicating the relative position of various body parts, surgical implants, and instruments. In particular, the present invention relates to a reference frame and instrument guide frame for use in an image guided surgery navigation system.

2. Background of Related Art

In image guided medical and surgical procedures, images, obtained either preoperatively or intraoperatively (i.e., prior to or during a medical or surgical procedure), are used to aid a doctor in guiding a surgical instrument. Computer assisted image guided medical and surgical navigation systems are known and are disclosed, for example, in U.S. Pat. No. 5,383,454 to Bucholz; U.S. Pat. No. 5,891,034 to Bucholz; U.S. Pat. No. 5,851,183 to Bucholz; U.S. Pat. No. 5,871,445 to Bucholz; PCT Application No. PCT/US94/04530 (Publication No. WO 94/24933) to Bucholz; PCT Application No. PCT/US95/12984 (Publication No. WO 96/11624) to Bucholz et al.; and U.S. patent application Ser. No. 08/623,956 to Foley et al., the entire disclosures of which are incorporated herein by reference.

In general, these image guided systems use images of a body part or other surgical object, obtained from a scan, such as CT or MRI scan, taken before surgery to generate images on a display screen during surgery. The images of the body are correlated with a synthesized image of a surgical instrument and are used to produce, on a display screen, a real-time representation of the surgical instrument used by a surgeon with respect to the body. Prior to the scan of the body to produce body images, markers such as fiducial scanning markers are placed on the parts of the body to be scanned in order to produce fiducial image points on the scanned part of the body. The locations of the fiducial markers represented on the scanned image are correlated with the fiducial scanning markers on the body to provide a coordinate registration to be used by the computer system in determining the relative location of the various objects that the computer tracks. The surgical instrument is also registered with respect to the fiducial scanning markers, as known to those skilled in the art, by positioning the surgical instrument at each of scanning markers and recording the relative location of the instrument and markers.

During surgery, the relative locations of the body part being examined and the surgical instruments are displayed on a display screen of the computer system by detecting the location of tracking markers on the instruments or body. An array of sensors, such as cameras, are used to track the location of the tracking markers, which in turn are interpreted by the computer system to produce images on the display screen that correspond to the positions of the body part and surgical instruments. Such tracking markers can include, for example, LED arrays mounted on the body part and on an instrument.

SUMMARY

Generally, the present invention is directed to a method and system for aligning a surgical guide instrument over a burr hole in a patient's body. More particularly, the present invention is directed to a stand-alone instrument guidance unit that is attachable to a patient's body, particularly the skull. The guidance unit itself is equipped with tracking devices to permit a computer assisted image guided surgery system to track the position of the unit. Adjustments of a surgical instrument can be made in x, y, z and angular directions using the system and method of the present invention.

In one aspect of the present invention, an instrument guide unit includes an instrument guide for guiding a surgical instrument into the body of a patient and a base unit operative to be secured to the body in an area in which surgery is to occur. The base unit is coupled to the instrument guide. An adjustment mechanism, coupled to the base unit and the instrument guide, is operative to adjust the instrument guide in lateral directions with respect the surface of the area. The base unit may have tracking markers attached thereto.

The adjustment mechanism is operative to adjust the instrument guide in x and y directions. The adjustment mechanism includes an x direction control mechanism for adjusting the instrument in an x direction and a y direction control mechanism for adjusting the instrument in a y direction. The y direction control mechanism may be coupled to the x direction control mechanism.

The instrument adjustment unit may include a plate having a first attachment member for coupling to the adjustment mechanism. The adjustment member includes a mounting base that is operative to be coupled to the plate by the first attachment member. The plate has a second attachment member extending therefrom for anchoring in the body of the person at the area. An opening is defined through the first and second attachment members such that a surgical instrument may pass and extend through the first and second attachment members. The first attachment member has threaded grooves for screwing into a corresponding attachment member of the mounting base and the second attachment member has threaded grooves for screwing into the body at the area.

Another aspect of the present invention provides a method for guiding a surgical instrument for use in image guided surgery. The method includes determining the location of a stand-alone instrument guidance unit attached to the skull of a patient by sensing signals from tracking markers coupled to the instrument guidance unit and determining the location and orientation of an instrument guide of the guidance unit. This method also includes displaying image representations of the body part of interest relative to a trajectory line defined by the orientation of the instrument guide during a surgical procedure.

The method may also include determining the orientation of the instrument guide as the instrument guide is pivoted. The orientation of the instrument guide is determined by detecting the location of tracking markers on the instrument guide. The x and y coordinate positions of the instrument guide may be adjusted with respect to the body part, such as the skull. The z coordinate position of a surgical instrument inserted in the instrument guide may also be adjusted.

BRIEF DESCRIPTION OF THE DRAWINGS

FIG. 5d is a top view of the adjustable guidance base taken along line 5d—5d of FIG. 5a;

DETAILED DESCRIPTION

Figure 1:
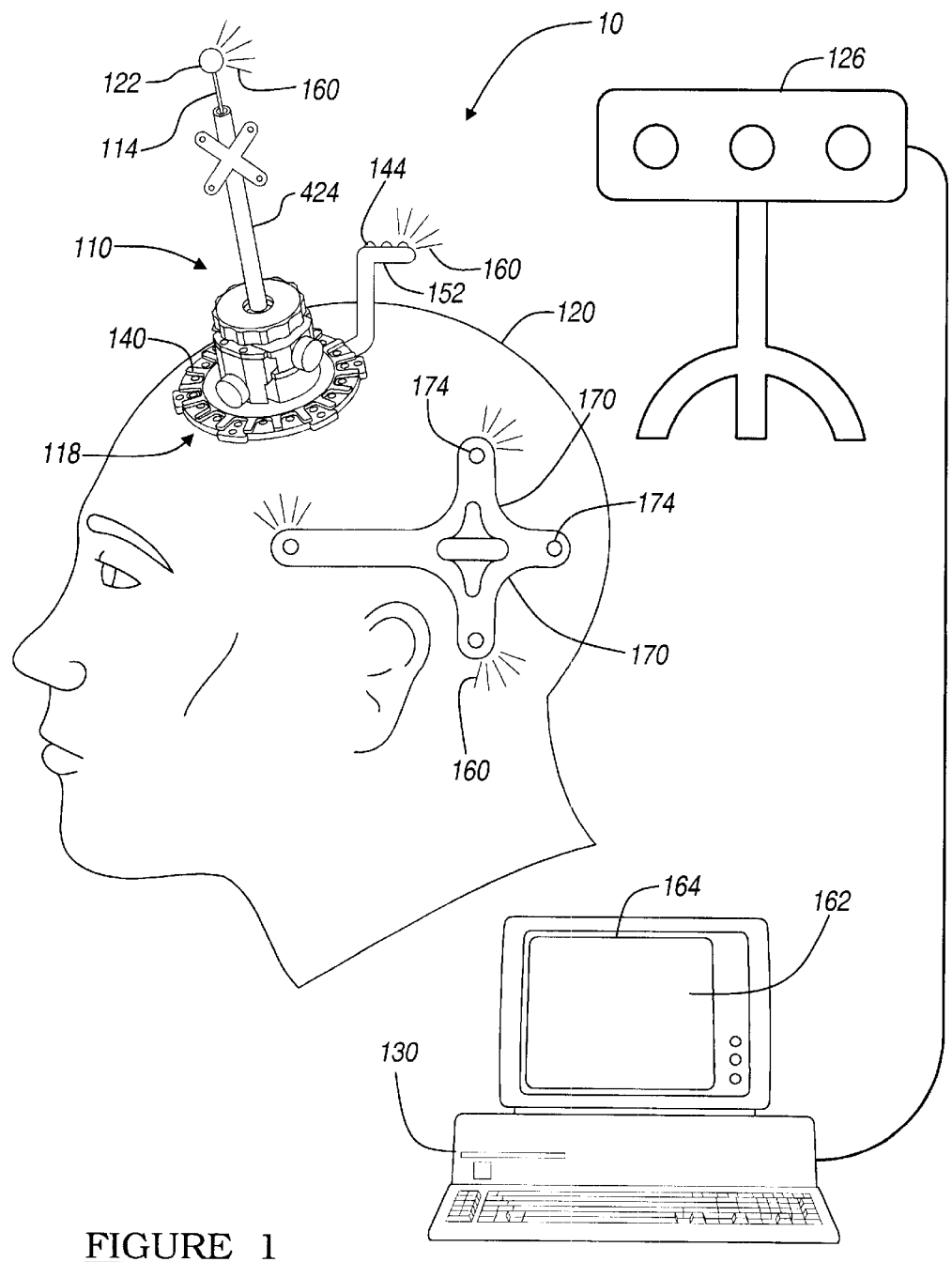
FIG. 1 is a diagram of an image guided system consistent with an embodiment of the present invention.

A description of embodiments of the present invention are described in connection with the accompanying figures. Referring to FIG. 1, an image guided stereotactic surgery system and method consistent with the present invention is illustrated. The system 10 includes an instrument guide unit 110 that is used to guide a surgical instrument 114 during a surgical operation, such as for example an electrode for deep brain stimulation. The instrument guide unit 110 is placed over a burr hole 118 that is cut in the patient's skull 120 to enable operation on the patient's brain. Surgical instrument 114 includes a tracking marker, such as LED 122, that is detected or monitored by a sensor array, such as camera array 126, as described herein. The instrument guide unit 110 may include a mini-reference position frame 152. The mini-reference position frame 152 contains tracking markers, such as LEDs 144, that are also tracked or monitored by the camera array 126. The mini-reference position frame 152 provides a point of reference for locating and imaging the skull. A mini-reference position frame 170 may also be attached to the patient's skull 120 to provide a point of reference for locating and imaging the skull 120. The mini-reference position frame 170 includes LEDs 174. It should be appreciated by those skilled in the art that only one of the mini-reference position frames 152 or 170 is needed to establish reference coordinates for the patient's body, although both may be used.

The manner in which the camera array 126 tracks the positions of a reference frame and a surgical instrument are well known in the art and is therefore only described generally. The camera array 126 includes a plurality of cameras for tracking positions. The cameras can be CCD cameras to detect illumination emitted from the tracking markers. Based on the relative coordinates of the detected markers, the positions of objects can be determined and corresponding representations of the objects can be displayed on the monitor.

The camera array 126 is coupled to a computer system 130 that contains program modules that analyze the signals transmitted from the camera array to determine the relative position of the instrument guide unit, surgical instrument, and relevant body part during a surgical procedure. The computer system 130 also contains an image data set of the body site of interest usually generated by some scanning technique such as CT scanning or MR. Computer system 130 produces a composite image of the surgical instrument and the image of the area in which a surgeon is operating representing the real time position of the surgical instrument and body part. The composite image varies in accordance with the movement of the patient and surgical instrument. An image guided surgery system suitable for use in connection with the present invention is the STEALTH STATION system available from Sofamor Danek, Inc., located in Memphis, Tenn.

During a surgical operation, the system 10 may include a tracking reference frame 170, which is attached to the patient's skull 120 and contains LEDs 174 that are tracked by the camera array 126. The reference frame 170 may be used as a scanning reference frame during the initial surgical preparations for the patient, with fiducial scanning markers replacing the LEDs 174. It should be understood by those skilled in the art that a separate scanning frame distinct from the reference frame 170 may be used. If distinct scanning and tracking reference frames are used, the frames preferably are the same shape or hold the markers in the same relative positions and mount to the same locations or mounting devices on the body.

Using a preoperative scan such as CT scans, a surgeon identifies a target point in the brain and determines an entry point through the patient's skull. The surgeon plans a surgical trajectory using a computer display of an image 164. The selected target and entry points are stored in a database record for the patient along with the selected surgical trajectory. The orientation of a surgical trajectory line normal to base plate 140 is adjustable within a surgical trajectory cone forming a solid angle of approximately 45 degrees.

After the surgeon attaches the instrument guide unit 110 to the patient's skull, the instrument guide unit 110 is operative to aid in adjusting the x, y, and z coordinates for a surgical instrument as well as the angular trajectory of the instrument. As described in more detail herein and shown in FIG. 4a, instrument guide unit 110 includes a base plate 140 to which LEDs 144 may be coupled by means of a mini-reference position frame 152. After attaching instrument guide unit 110, the surgeon can adjust the orientation of the instrument guide unit 110 and the surgical instrument 114. The surgical instrument 114, including an instrument LED 122 fixed relative to the instrument, passes through an opening that extends through the length/depth of the instrument guide unit 110. The z-axis of the surgical instrument is adjusted by advancing or withdrawing the surgical instrument 114 through a guide tube 424. At the same time computer system 130 tracks the depth of instrument 114 by tracking the position of instrument LED 122. If desired, the position of the instrument, along the z-axis, may be fixed in place by use of a set screw in the tube or other suitable means. Surgical instrument 114 is constrained to follow a fixed trajectory through a central opening through adjusted base plate 140.

Computer system 130 tracks the location and orientation of base plate 140 and the displacement of surgical instrument 114 by tracking markers such as the LEDs in a conventional manner. It should be appreciated that various methods of tracking the position of the surgical instrument may be used. For example, a transducer or magnetic sensing device may be used to track the position of a position indicator attached to the surgical instrument. In the system and method of the present invention, it is important that the LEDs of the reference frame, instrument guide unit, and surgical instrument remain in the visual field of the cameras of the camera array 126 to help produce consistent and accurate locations and representations of objects in the computer system 130. The orientation and distance of the LEDs should be maintained within a range sufficient to ensure accurate and consistent readings. The computer system 130 computes the position of surgical instrument 114 in the coordinate system established during the initial scanning phase. The real time coordinate system can be correlated to the coordinate system established during scanning through use of the reference frame 170 described herein, or other techniques such as those disclosed in U.S. Pat. No. 5,383,454 to Bucholz; U.S. Pat. No. 5,891,034 to Bucholz; U.S. Pat. No. 5,851,183 to Bucholz; and U.S. Pat. No. 5,871,445 to Bucholz. Computer system 130 displays on display monitor 164 a composite image 162 showing the position and orientation of surgical instrument 114 with respect to the patient's head. The surgeon uses the images produced on display 164 to position surgical instrument 114 along the predefined trajectory. When using a system or method consistent with the principals and methods of the present invention, a patient's head does not have to be locked into a stationary position.

Figure 2:
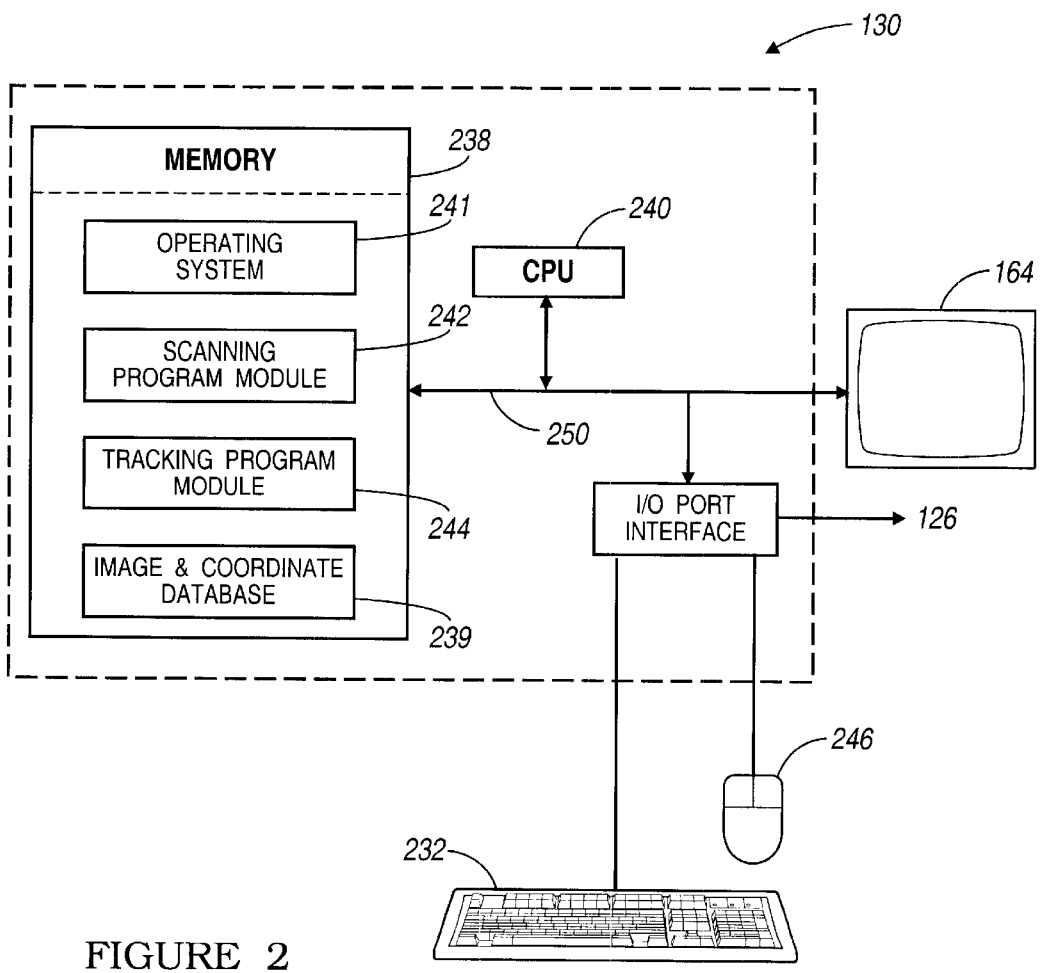
FIG. 2 is a block diagram of a computer system used in connection with the present invention.

Referring to FIG. 2, the general components and modules of a computer system 130 used to perform various processes of the present invention is described. Although a STEALTH STATION image guided system manufactured by Sofamor Danek has been identified, it will be appreciated that the present invention may be utilized in other types of computer systems. One aspect of the computer system includes a graphical user interface system operating in conjunction with a display screen of the display monitor 164. The graphical user interface system is preferably implemented in conjunction with the operating system for displaying and managing the display objects of the system. The graphical user interface system is implemented as part of the computer system 130 to receive input data from a conventional keyboard 232, a mouse 246, a camera array 126 or other input device. For simplicity of the drawings, many components of a standard computer system have not been illustrated such as address buffers, memory buffers and other standard control circuits because these elements are well known and illustrated in the prior art and are not necessary for the understanding of the present invention.

A computer program used to implement the various steps of the present invention is generally located in the memory unit 238, and the processes of the present invention are carried out through the use of a central processing unit (CPU) 240. Those skilled in the art will appreciate that the memory unit 238 is representative of both read-only memory and random access memory. The memory unit also contains a database 239 that stores the data, for example image data, and tables used in conjunction with the present invention. The CPU 240, in combination with computer software, such as an operating system 241, a scanning program module 242, and tracking program module 244, controls the operations and processes of the computer system 130. The processes implemented by the CPU 240 may be communicated as electrical signals along the bus 250 to an input/output device via input output interface 126. The scanning program module 242 performs the processes associated with creating a coordinate reference system and reference images for use in connection with the present invention and as known to those skilled in the art. The tracking program module 244 performs the processes necessary for tracking objects in an image guided system as described herein and as known generally to those skilled in the art.

Figure 3A:
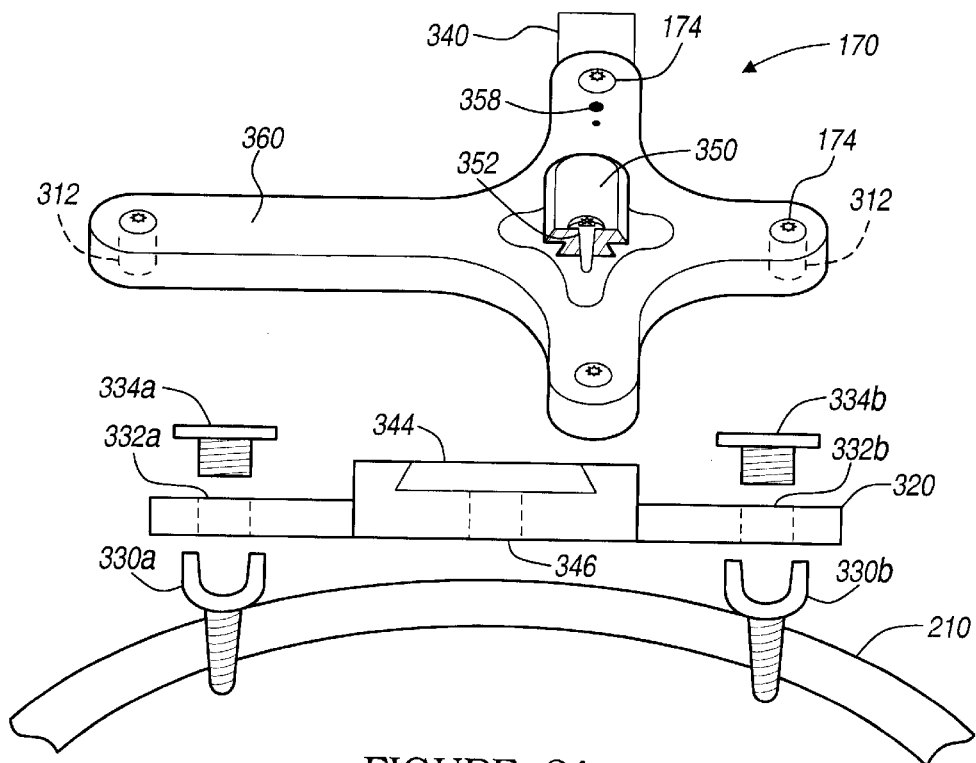
FIG. 3a is an exploded view of a reference frame and anchor bar consistent with an embodiment of the present invention.

Referring to FIG. 3a, a rigid mini-reference position frame 170 is shown in an exploded view. The mini-reference position frame 170 is made of a material that will not interfere with either the scanning operation or the tracking operation that is to be performed. One material suitable for constructing frame 170 when MRI scans are to be used is polycarbonate. The recesses 312 into which the LEDs 174 or fiducial scanning markers are inserted are preferably "snap-in" recesses that enable the LEDs 174 or fiducial scanning markers to be snapped into place on the mini-reference position frame 170. The design of the mini-reference position frame 170 has a four pronged star shape. The mini-reference position frame 170 has an elongated portion 360 that preferably extends over and to a position in front of the patient's ear (FIG. 1).

Figure 3B:
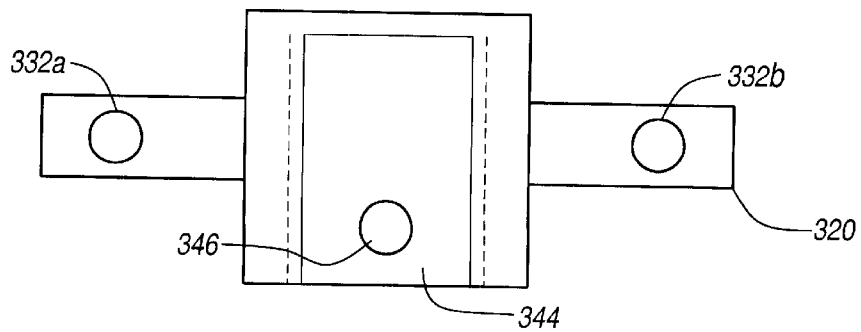
FIG. 3b is a top view of an anchor bar used in connection with the present invention.

The mini-reference position frame 170 may be attached to an anchor plate 320 to secure the mini-reference position frame 170 to the skull 120 of the patient. The anchor plate 320 is secured to the skull 120 by securing the anchor plate to anchor screws 330a and 330b that are screwed into selected locations in the skull 120. The anchor plate 320 has screw holes 332a and 332b defined therein through which plate screws 334a and 334b are positioned to screw into the anchor screws 330a and 330b. The anchor screws 330a and 330b are preferably located in positions that are directly beneath the axis of the elongated section 360 or that are parallel and in close proximity to the axis. The elongated portion 360 is positioned toward the front of the head and extends above the patient's ear where soft tissue thickness is relatively thin and the skull thickness is near a maximum. The relatively thin tissue thickness enables the anchor screws 330a to be implanted easily when local anesthetics are used. Referring also to FIG. 3b, a top view of the anchor plate 320 is illustrated.

The mini-reference position frame 170 is illustrated with LEDs 174 secured therein. The LEDs 174 may be screwed, snapped, or otherwise recorded into place as known by those skilled in the art. The mini-reference position frame 170 may also serve as a scanning frame by replacing the LEDs with fiducial scanning makers within the mini-reference position frame 170. The mini-reference scanning frame 170 is attached to the anchor plate 320 by sliding the reference frame slide member 340 into the anchor plate locking cavity 344. The anchor plate locking cavity 344 has a screw hole 346 defined therein for receiving a screw 350 that is inserted through a screw hole 352 of the reference frame slide member 340. The reference frame slide member 340 may be integrally molded as part of the mini-reference position frame 170 or may be secured to the reference frame by welding or by screws 358.

Figure 4A:
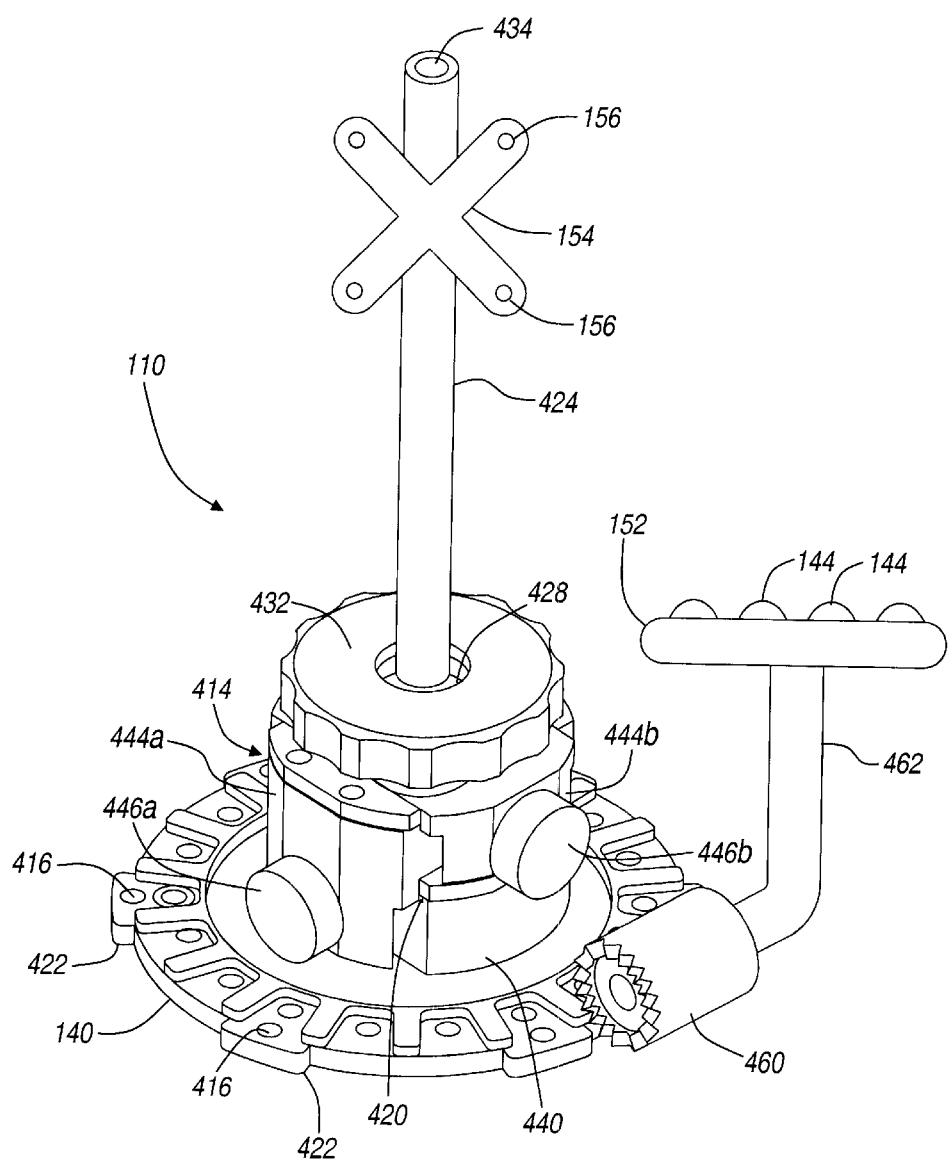
FIG. 4a is a view of a base plate and an adjustable base of an instrument guide unit.

Referring to FIG. 4a, a description of the instrument guide unit 110 is provided. The instrument guide unit 110, as discussed above, is a stand-alone unit used to aid a surgeon in guiding a surgical instrument to a target point. That is, the instrument guide unit 110 may connect directly to the patient's skull without support from another frame structure. The instrument guide unit 110 includes an adjustable guidance base 414 coupled to a base plate 140. The base plate 140 may be secured to the skull of a patient by screws that pass through mounting holes 416 of mounting tabs 422.

The instrument guide unit 110 includes a guide tube 424 or upper portion that is used to establish x, y, z and angular coordinates for a surgical instrument during operation on a patient. The guide tube 424 is connected to guide ball 428. The guide ball 428 may pivot within the adjustable guidance base 414 to enable the guide tube 424 to be positioned at selected angles. The guide ball 428 may be moved or translated in x and y directions within the adjustable guidance base 414 to provide x and y adjustable positions for the guide tube 424 attached to the guide ball 428. The movement of the ball in the x and y directions control the x and y coordinates of the trajectory line that a surgical instrument will traverse when operating on a patient. The guide ball 428 is secured within the adjustable guidance base 414 by a locking plate 432. The locking plate 432 may be rotated into a locking position to lock the guide ball 428 into a fixed position to maintain a selected trajectory. The locking plate 432 locks the guide ball 428, and consequently the guide tube 424, in place when the locking plate 432 is screwed firmly down onto the ball. When the locking plate 432 is screwed firmly down onto the ball 428, the ball 428 is clamped into a stationary position within the adjustable guidance base 414. A surgical instrument 114 (FIG. 1), including an instrument LED 122 (FIG. 1), is free to pass through a central opening 434 of the guide tube 424. By locking the guide ball 428 in a selected position, the surgical instrument 114 is constrained to follow the fixed trajectory through an opening of the base plate 140.

The adjustable guidance base 414 includes several components. These components include a guidance mounting base 440, an x-direction translation base 444a and a y-direction translation base 444b. The translation bases 444a and 444b are adjustable in an x and y direction relative to the base plate 140. The translation bases 444a and 444b include adjustable translation knobs 446a and 446b, respectively. The adjustable translation knobs 446a and 446b enable the x-direction translation base 444a and y-direction translation base 444b to be adjusted in the x and y directions, respectively. Thus, the adjustable guidance base 414 is adjustable in the x and y directions to control the x and y position of the guide ball 428 and guide tube 424. The combination of an x and y translation bases form an x and y translation table for setting the x and y coordinate locations of the guide ball 428. By turning the adjustable translation knobs 446a and 446b in a clockwise or counter-clockwise direction, the guide ball 428 moves in the corresponding direction, along the axis of the adjustable translation knob.

As generally discussed above, the camera array 130 tracks or determines the position of objects, such as a surgical instrument, surgical structure or body part, by identifying reference points established on the objects. Particularly, the position of LEDs are tracked as reference points for objects being monitored by a system or method operating according to the present invention. The position of relevant objects may be tracked by attaching a mini-reference position frame to the object. A mini-reference position frame 154 may be permanently attached or removably attached to a selected object, such as the guide tube 424. The mini-reference position frame 154 includes a plurality of LEDs 156 that may be tracked by the camera array described above. By detecting the locations of the LEDs 156 on the mini-reference position frame 154, the computer system may track the position of the guide tube 424 for calculating coordinates of the guide tube 424 according to the present invention. The mini-reference position frame 154 may be attached to the guide tube 424 by suitable clamping means as known by those skilled in the art.

In addition to tracking the position of the guide tube 424, the position of the base plate 140 may also be tracked. The position of the base plate 140 is tracked by determining the position of a mini-reference position frame 152. The mini-reference position frame 152 has LEDs 144 positioned thereon that serve as coordinate reference points that are tracked by the computer system via the camera array 130 (FIG. 1). The mini-reference position frame 152 is attached to the base plate 140 in a fixed relationship. The mini-reference position frame 152 may be connected to base plate 140 through starburst connector 460. Starburst connector 460 may be removably or fixedly attached to the base plate 140. Starburst connector 460 has an opening to fixedly receive an extension arm 462 that supports mini-reference position frame 170. The mini-reference position frame 152, which is mounted in a stationary position relative to the patient's head throughout the surgical procedure, provides a reference point for base plate 140. The mini-reference position frame 152 thereby provides a reference location for the burr hole in the patient's skull and allows the position of the burr hole and the patient's skull to be continuously tracked by the computer station.

Alternatively, a tracking reference frame, such as tracking reference frame 170, may be used to track the location of the body part. In that case, the position of reference frame 170 affixed to the patient's skull may be registered with respect to the burr hole by placing a registration probe having an LED or other tracking element at the site of the burr hole. The computer system can then determine the position of tracking reference frame 170 with respect to the burr in the patient's skull.

During a surgical procedure, a surgical instrument 114 is passed through a central opening of base plate 140 into the brain or other area of interest. Adjusting the angle of the guide tube 424 adjusts the trajectory of the guide tube 424 and the instrument passing through the guide tube. Adjusting the orientation of adjustable guide base 414 adjusts the x and/or y position of the guide tube and consequently the trajectory of the guide tube. Moving the surgical instrument up or down within the guide tube 424 adjusts the z-position of the surgical instrument. In all orientations, the trajectory passes through a single point on the central axis of base plate 140 near the surface of the skull.

Figure 4C:
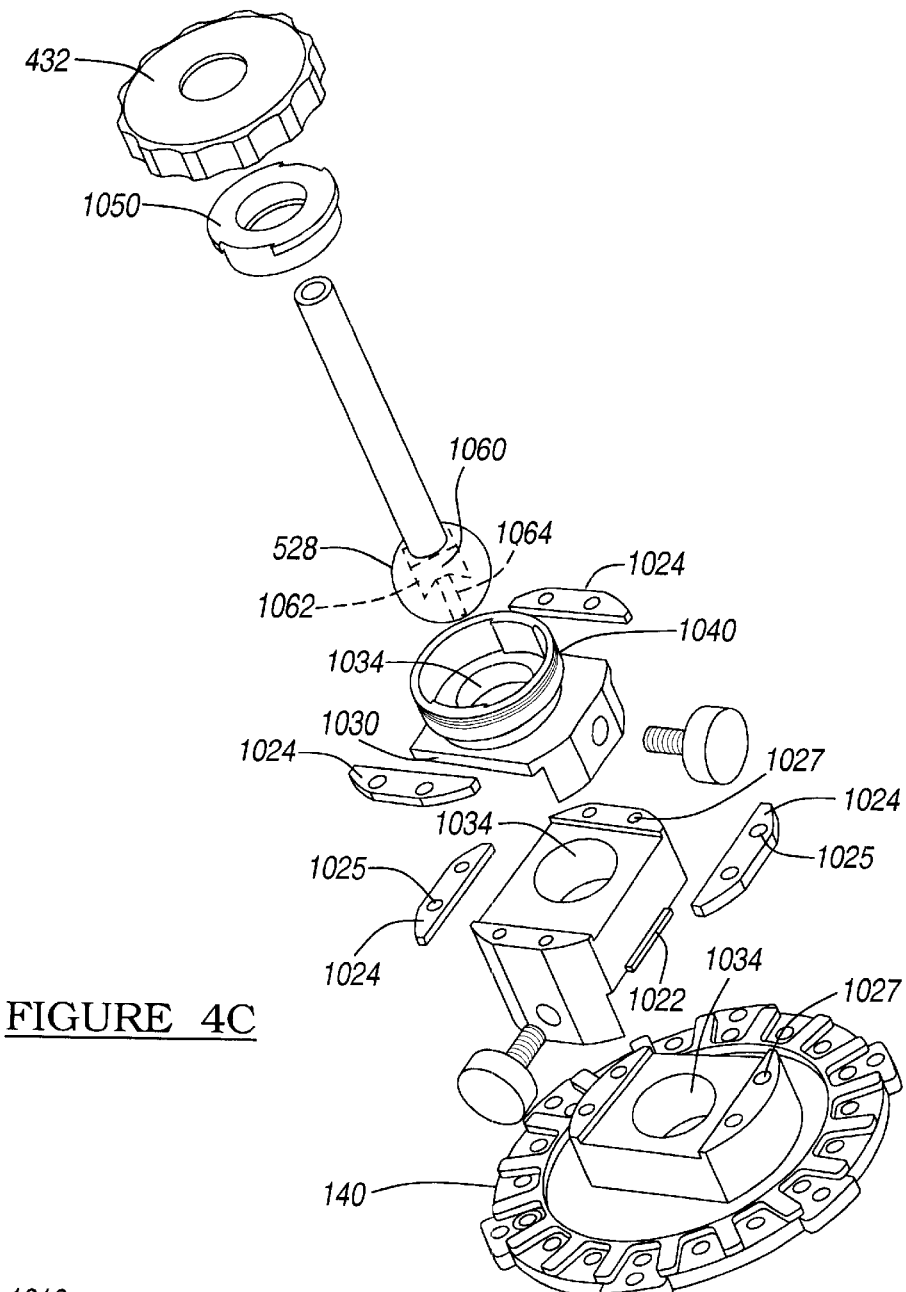
FIG. 4c is an exploded view of the adjustable base of an instrument guide unit.
Figure 4B:
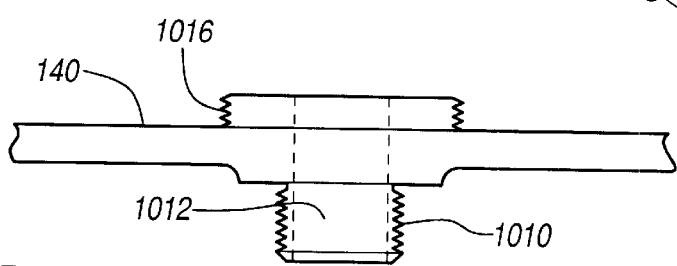
FIG. 4b is a side view of the base plate.

Referring to FIG. 4b, a side view of the base plate 140 is illustrated. As shown in FIG. 4b, the base plate 140 has a lower screw portion 1010 coupled to the lower side of the base plate 140. The lower screw portion 1010 has an opening 1012 defined therein that extends up through the base plate 140 and through an upper screw portion 1016. The upper screw portion 1016 provides a mounting thread for the guidance mounting base 440. The guidance mounting base 440 is firmly secured to the base plate 140 by screwing the guidance mounting base 440 on to the upper screw portion 1016. The mounting base 440 is stationary relative to the base plate 140 and has an opening 1034 defined therein through which a surgical instrument may pass.

Referring to FIG. 4a and FIG. 4c (an exploded view of the instrument guide unit 110), mounting base 440 provides a mechanism for attaching and locking into place the x-direction translation base 444a to the mounting base. The mounting base 440 has x-translation base mounting channels 420 that receives x-direction translation base mounting extensions 1022 (FIG. 4c) that extend from the x-translation base 444a. The x-translation base mounting channel 420 is formed when a channel top piece 1024 (FIG. 4c) is secured to the mounting base 114 by screws positioned through screw holes 1025 and 1027 (FIG. 4c). The x-translation base mounting extensions 1022 which extend from the x-direction translation base 444a slide into the x-base mounting channel 1020 for coupling to the guidance mounting base 440.

Translation base 444a also has a y-translation base mounting channel 1026 for mounting the y-direction translation base 444b to the x-direction translation base 444a. The y-direction translation base 444b has a y-translation base channel mating extension 1030 that extends therefrom. The y-translation base channel mating extension 1030 is designed to slide into the y-translation base mounting channel 1026 to provide a snug fit for the extension 1030. The extensions 1022 and 1030 may slide back and forth in the respective channels when the corresponding translation knob 446 is turned or screwed in or out. It should be appreciated that each of the base members has an opening 1034 defined therein to allow the surgical instrument to pass from the guide tube and down through the opening 1012 of the base plate 140.

The y-direction translation base 744b includes a locking plate screw portion 1040 onto which the locking plate 432 is screwed. However, before the locking plate 732 is screwed onto the locking plate screw portion 1040, the guide tube 424 and guide ball 428 are positioned into a guide pivot member located between the bases 444a and 444b. The opening of the locking plate 432 is positioned over the guide tube 434. The mini-reference position frame 152 is then coupled to the guide tube 424 as illustrated in FIG. 4a.

The guide ball 428 has an opening 1060 defined therein. The opening 1060 narrows in diameter from the upper portion to the lower portion of the guide ball 428. Particularly, the opening 1060 has a wide diameter shelf 1062 that is slightly larger than the diameter of the guide tube 424 to enable the guide tube 424 to be positioned on the shelf 1062. A lower portion 1064 of the opening 1060 has a diameter that is more narrow than the diameter of the guide tube 424. The narrow diameter of the lower portion 1064 of the opening 1060 prevents the guide tube 424 from sliding entirely through the opening 1060 of guide ball 428 and enables the surgical instrument to pass through.

In use, the mounting base 440, translation bases 444a and 444b, guide tube 424 with guide ball 428 and locking plate 432 assemblies are assembled as a unit prior to the beginning of the surgical procedure. The base plate 140, however, is not typically assembled as part of the instrument guide unit 110 prior to surgery. The base plate 140 is preferably mounted to the patient's skull without the adjustable guidance base 414 attached. The base plate 140 is secured to the skull over the burr hole in the patient's skull using three or more bone screws that pass through mounting holes 416 through mounting tabs 422. By not attaching the mounting and translation portions of the instrument guide unit 110 to the base plate 140 prior to the base plate being screwed into the patient's skull, the surgeon can more precisely and easily screw in the base plate 140 to the patient's skull at the selected location.

Figure 5D:
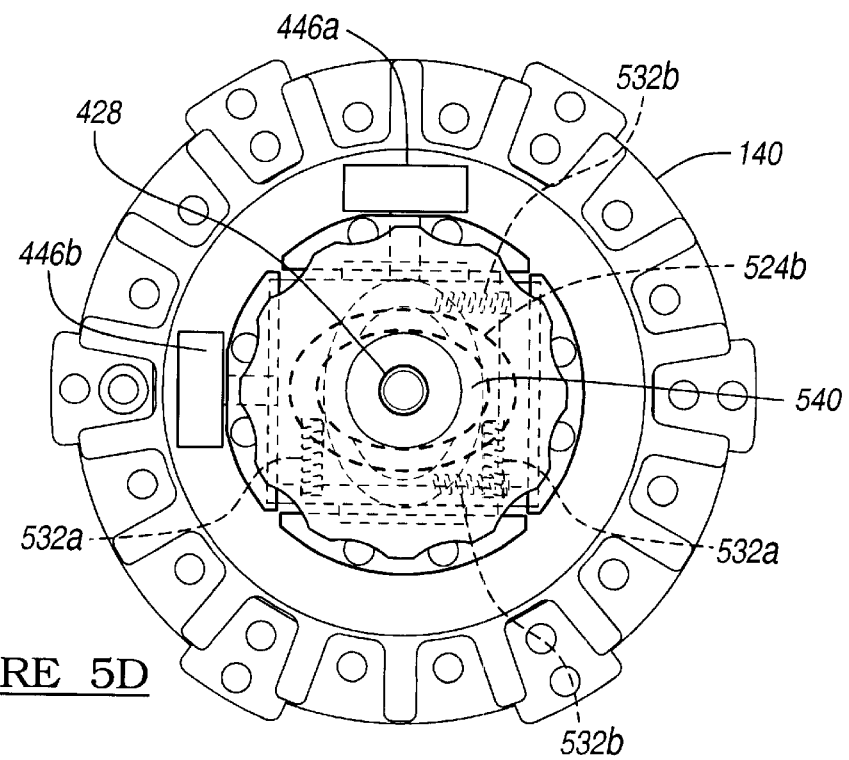
Figure 5A:
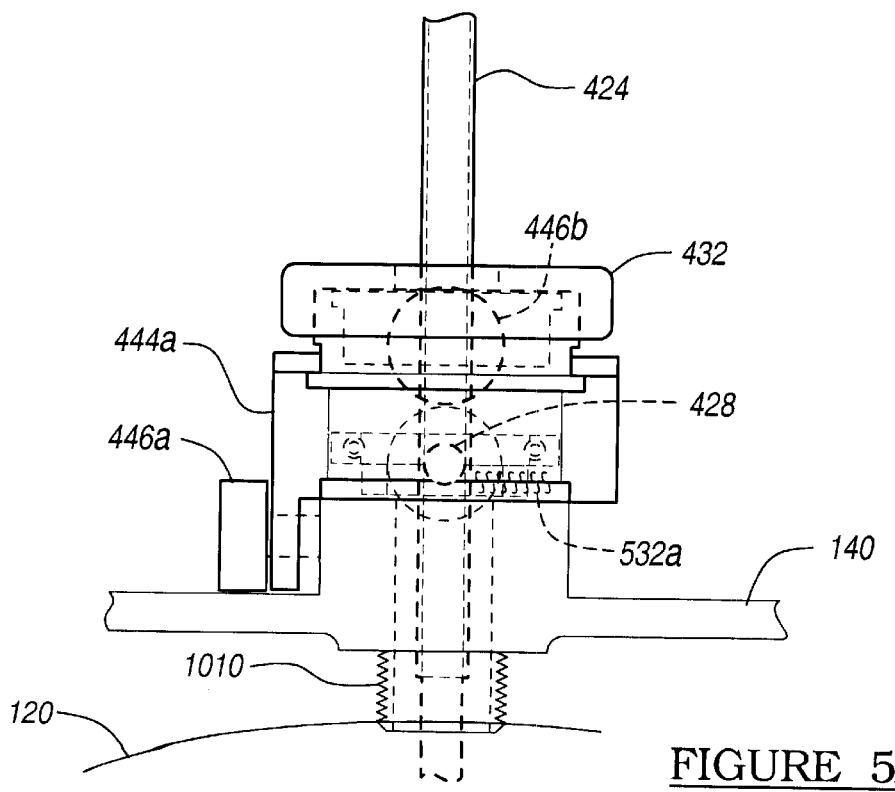
FIG. 5a is a side view of the instrument guide unit showing components that move a guide tube in the x and y direction.
Figure 5B:
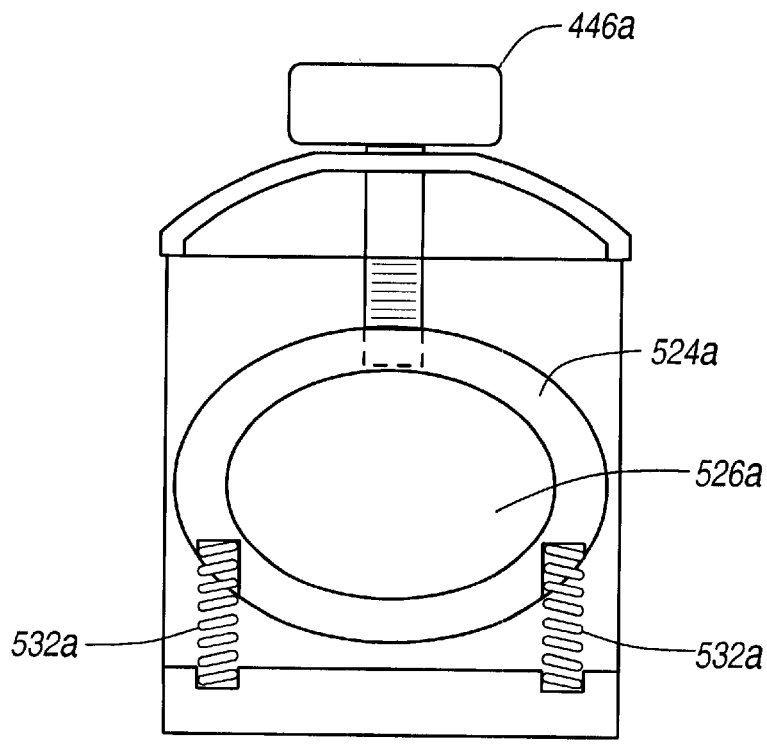
FIG. 5b is a top view of the x translation base components.

Referring to FIG. 5a, a side view of the instrument guide unit 110, as attached to a patient's skull, is illustrated. In FIG. 5a, the mechanisms used to control movement of the guide tube 424 and guide ball 428 in the x and y directions are illustrated. FIG. 5a illustrates a side view of the instrument guide unit 110 with the component parts of the x and y translation table shown by the hidden on dashed lines. The guide ball 428 is moved in the x direction when the translation knob 446a is rotated. When the translation knob 446a is rotated, the screw portion 1120 of the translation knob 446a rotates within an oval shaped guide ring 524a. The manner in which the translation knob and guide ring operate to move in the x direction is illustrated in FIG. 5b. FIG. 5b is a top view of the x translation base 444a components.

When the translation knob is rotated, the guide ring 524a is either pulled toward the side of the translation base on which the knob is located or it is pushed away from the side of the translation base on which the knob is located. A portion of the guide ball 428 rests within the opening 526a of the guide ring 524a. Thus, when the guide ring 524a is moved by rotation of the translation knob 446a, the guide ball moves in the fixed direction that corresponds to the direction of rotation of the translation knob 446a. Springs 532a are attached to the guide ring 524a on each side of the opening 526a defined in the guide ring. The springs 532a are attached to the wall of the translation base 444a that is opposite of the wall of the translation base 444a on which the translation knob 446a is located. The springs 532a help to reduce backlash or stabilize the guide ring when the guide ring is moved.

Figure 5C:
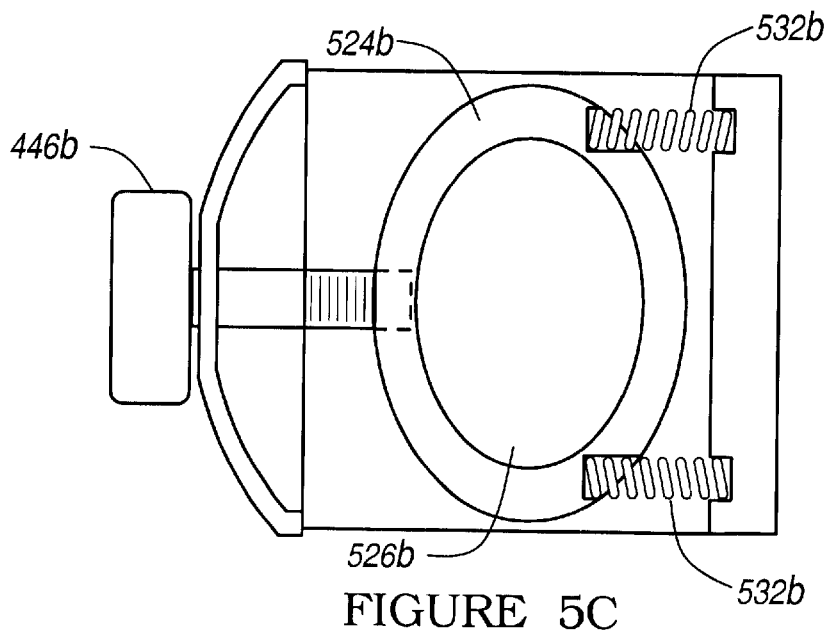
FIG. 5c is a top view of the y translation base components.

Referring to FIG. 5c, a top view of the y translation base including its y direction translation components is illustrated. The operation of the guide ring 524b and translation knob 726b and springs 532b operate in the same manner as the components discussed in connection with FIG. 5b except that the direction of movement is in the y direction.

The oval shape of the opening 526a and 526b of the guide rings 524a and 526b enable the movement of the guide ball 428 in the desired direction. Referring to FIG. 5d, the guide ball 528 fits firmly against the walls of the opening 526b that are perpendicular to the direction in which the translation knob 446b moves. However, spaces 540 are defined between the spherical guide ball 428 and the oval shape sides of the walls of the opening 526a that are perpendicular to the x direction of movement. Thus, when the translation knob 446a is rotated within the translation base 444a, the guide ball 428 is free to move in the x direction in the spaces 540 illustrated. It should be appreciated that spaces similar to the spaces 540 are defined between the guide ball and each guide ring 524b in the corresponding direction.

Figure 6:
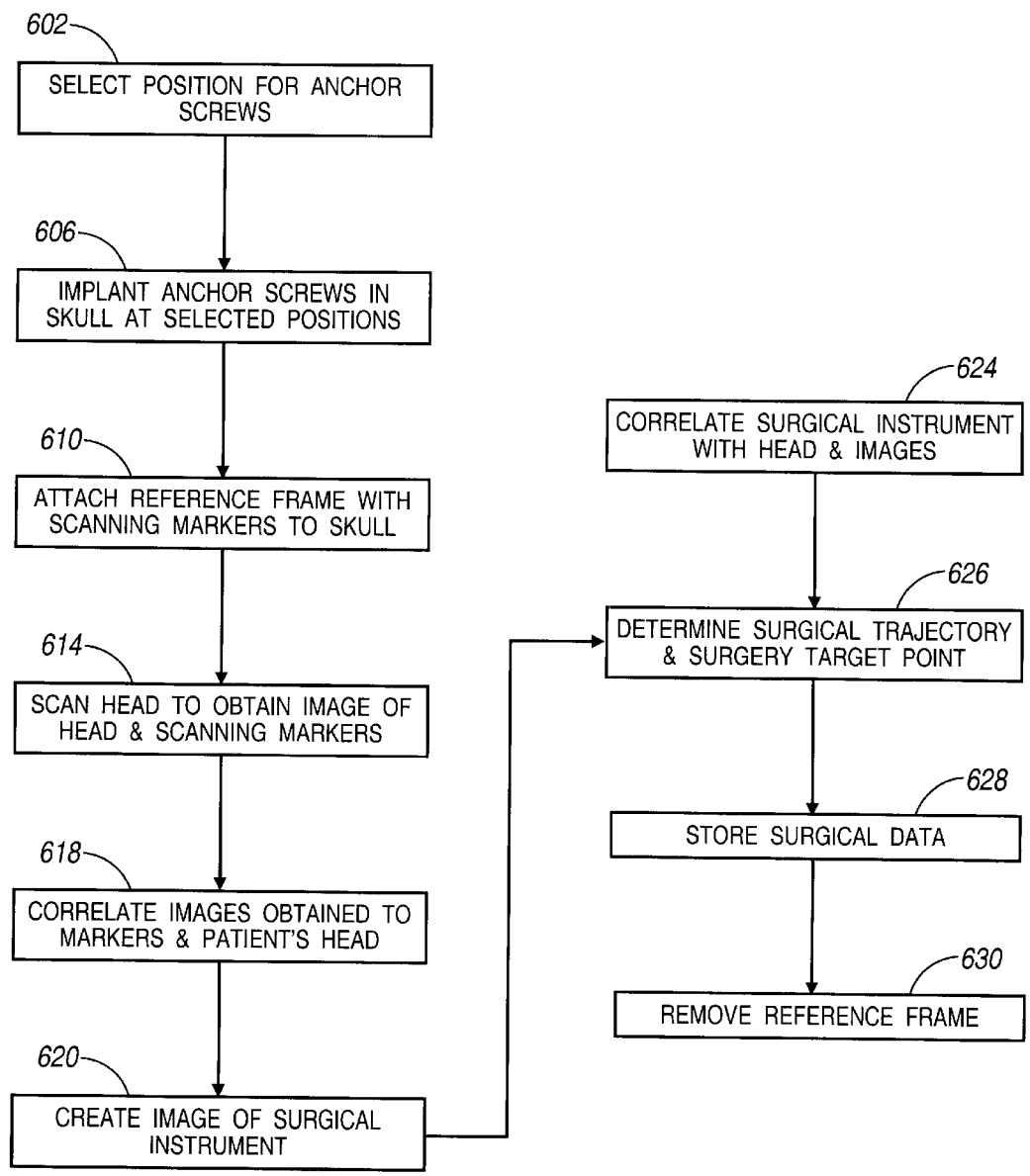
FIG. 6 is a flow diagram of scanning phase processes associated with image guided surgery.

Referring to FIG. 6, the processes or steps associated with pre-surgery procedure is illustrated. To begin, a surgeon selects (step 602) a position for anchor screws to be inserted into a patient's skull for securing a reference frame to the patient's skull. The anchor screws are implanted in the patient's skull (step 606) at the selected positions. A reference frame, with fiducial scanning markers, is attached to the person's skull using the implanted anchor screws. The patient's head is then scanned (614) to obtain an image of the head and the fiducial scanning markers placed on the patient's body. After scanned images have been obtained, the images are correlated (618) with the scanning markers located on that patient's body or head to provide an appropriate registration or coordinate frame of reference for use in the tracking stage of surgery. An image of the surgical instrument is created (620) for use during the tracking stage. The image of the surgical instrument is correlated with various positions on the head, such as at the fiducial scanning markers, so that the computer system can provide accurate depictions of the location of the surgical instrument with respect to the head or body during a surgical procedure. A surgeon determines (step 626) the surgical trajectory that the surgeon will take to reach the target point of the surgery. As known to those skilled in the art, the manner in which a surgical trajectory is determined is known in the image guided surgery art and is not discussed in detail herein. After the surgeon determines the surgical trajectory, all information regarding the coordinate reference points, images, and surgical trajectory are stored to the memory of the computer system and the database for the specific patient (step 628). If desired, the surgeon may remove the reference frame (step 630) from the patient's head.

Figure 7:
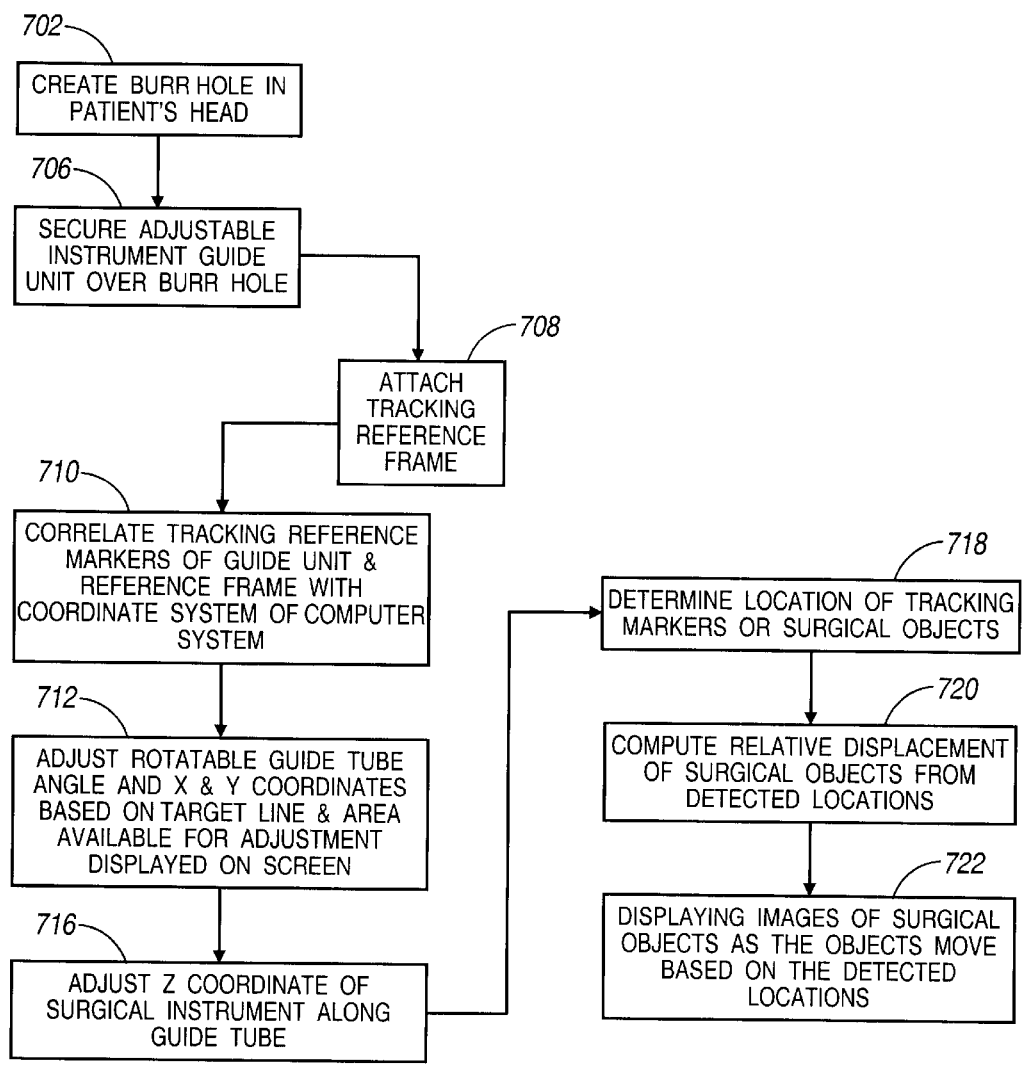
FIG. 7 is a flow diagram of processes associated with the tracking phase of an image guided surgical procedure.

Referring to FIG. 7, the processes or steps associated with the tracking or surgical phase is discussed. A surgeon creates a burr hole (step 702) in the patient's head. After the burr hole has been created in the patient's head, the surgeon secures (step 706) the adjustable instrument guide unit within the burr hole by screwing the lower screw member of the adjustable guide unit into the patient's head. The surgeon also attaches the tracking reference frame (step 708) to the patient's skull for accurately tracking movements of the patient's head.

After the various markers have been positioned on a patient's head, the computer system correlates the tracking reference markers with the coordinate system of the computer system (step 710). The angle and x and y coordinates of the guide tube may be adjusted based on the target line determined by the surgeon and the defined area for which adjustment of the guide tube may occur (step 712). As a surgeon adjusts the guide tube, image information reflecting the change is displayed on the display screen. The surgeon may adjust the z-coordinate of the surgical instrument by moving the surgical instrument up and down the guide tube (step 716). During the tracking phase, the computer system continuously determines the location of tracking markers from surgical objects (step 718). The computer system also computes (step 720) the relative displacement of the surgical object being tracked from the detected locations. The images of the surgical objects are displayed as the objects are moved during a surgical procedure (step 722). The images are displayed based upon the locations detected for the tracking markers.

While this invention has been described in connection with LEDs and a camera array, it should be recognized that other tracker elements and sensor arrays known in the art could be used, such as for example sonic, optic, or electromagnetic, as well as optical reflectors and a corresponding camera system. It should be appreciated that many modifications and adaptations can be made to the embodiments described herein without departing from the scope of the appended claims.

What is claimed is:

1. A method for guiding a surgical instrument for use in image guided surgery, comprising the steps of:

determining the location of a stand-alone instrument guidance unit attached to the skull of a patient by sensing signals from tracking markers coupled to the instrument guidance unit;

determining the orientation of an instrument guide of the guidance unit; and displaying image representations of the skull relative to a trajectory line defined by the orientation of the instrument guide during a surgical procedure.

2. The method of claim 1 further comprising determining the orientation of the instrument guide as the instrument guide is pivoted.

3. The method of claim 2 wherein said orientation of the instrument guide is determined by detecting the location of tracking markers on the instrument guide.

4. The method of claim 1 comprising adjusting the x and y coordinate positions of the instrument guide with respect to the skull.

5. The method of claim 4 comprising adjusting the z coordinate position of a surgical instrument inserted in said instrument guide.

6. The method of claim 5 wherein positional movement of the surgical instrument in the z direction is tracked by sensing the location of a transducer coupled to the surgical instrument.

7. The method of claim 6 wherein said transducer is an optical transducer.

8. The method of claim 6 wherein said transducer is a magnetic transducer.

* * * * *

UNITED STATES PATENT AND TRADEMARK OFFICE
CERTIFICATE OF CORRECTION

PATENT NO. : 6,491,699 B1
DATED : December 10, 2002
INVENTOR(S) : Henderson et al.

It is certified that error appears in the above-identified patent and that said Letters Patent is hereby corrected as shown below:

<u>Title page,</u>
Item [57], ABSTRACT,
Line 3, "a aligning" should be -- aligning a --.

Item [56], References Cited, delete second occurrence of "5,921,922 7/1999 Costales et al".

<u>Column 2,</u>
Line 21, after "respect" insert -- to --.

<u>Column 4,</u>
Line 6, "MR" should be -- MRI --.

<u>Column 5,</u>
Line 25, "principals" should be -- principles --.

<u>Column 9,</u>
Line 59, delete "on".

Signed and Sealed this

Twelfth Day of August, 2003

JAMES E. ROGAN
*Director of the United States Patent and Trademark Office*